United States Patent [19]

Markovac et al.

[11] Patent Number: 5,206,351

[45] Date of Patent: Apr. 27, 1993

[54] PROCESS FOR THE PREPARATION OF 2-AMINO (2,3,5-TRI-O-BENZYL-BETA-D-ARABINOFURANOSYL)ADENINE

[75] Inventors: Anica Markovac, Lathrup Village; Maurice P. LaMontagne, Farmington Hills, both of Mich.

[73] Assignee: Ash Stevens, Inc., Detroit, Mich.

[21] Appl. No.: 538,661

[22] Filed: Jun. 15, 1990

[51] Int. Cl.$^5$ ............................................. C07H 19/19
[52] U.S. Cl. ................................ 536/27.11; 536/27.22
[58] Field of Search ................................ 536/24, 26; 544/263–268

[56] References Cited

U.S. PATENT DOCUMENTS 4,210,745  7/1980  Montgomery ........................ 536/26
4,287,188  9/1981  Schaeffer ............................ 544/244

OTHER PUBLICATIONS

Anderegg et al. Anal. Chem. 56:1351–1355 (1984).

*Primary Examiner*—Johnnie R. Brown
*Assistant Examiner*—Gary L. Kunz
*Attorney, Agent, or Firm*—Ian C. McLeod

[57] ABSTRACT

A process for the preparation of 2-amino-9-(2,3,5-tri-O-benzyl-beta-D-arabinofuranosyl) adenine (V) is described. The process uses a protected 2,6-di(tri-alkyl-silylamino)-9-trialkylsilylpurine (II) which is reacted with protected chlorosugar 2,3,5-tri-O-benzyl-1-chloro-D-arabinofuranose (III) and then the protection groups are removed from the 2 and 6 positions. The process provides a 9-beta-D-arabinofuranosyl-2-fluoroadenine (VII) which is an antileukenine drug.

6 Claims, No Drawings

PROCESS FOR THE PREPARATION OF 2-AMINO (2,3,5-TRI-O-BENZYL-BETA-D-ARABINOFURANOSYL)ADENINE

BACKGROUND OF THE INVENTION (1) Field of the Invention

The present invention relates to an improved process for the preparation of 2-amino-9-(2,3,5-tri-O-benzyl-beta-D-arabinofuranosyl) adenine(V). In particular the present invention relates to a process which uses 2,6-di(-trialkylsilylamino)-9-trialkylsilylpurine (II) as a starting compound to produce compound (V).

(2) Prior Art

The compound (V) is used to prepare 9-beta-D-arabinofuranosyl-2-fluoroadenine (VII) or its 5'-phosphate derivative. Compound (V) has been prepared by the use of 2,6-dimethoxyacetamidopurine (A) as a starting material. The procedure involves reacting (A) with a 1-chlorosugar (B) having O-benzyl groups protecting the hydroxyl groups of the sugar. The 2,6-acyl groups are then removed with sodium methoxide and methanol to provide the amino groups in compound (V). The process thus requires relatively vigorous conditions to remove the acetoxy groups and the preparation of the acyl-protected purine is labor intensive. The result is a relatively expensive process.

OBJECTS

It is therefore an object of the present invention to provide a process for producing 2-amino-(2,3,5-tri-O-benzyl-beta-D-arabinofuranosyl) adenine (V) wherein the need to prepare the acyl-protected purine and vigorous conditions for the removal of the protecting group is eliminated. Further, it is an object of the present invention to provide a process which is simple and economical. These and other objects will become increasingly apparent by reference to the following description.

GENERAL DESCRIPTION

The present invention relates to a process for the preparation of the compound 2-amino-9-(2,3,5-tri-O-benzyl-beta-D-arabinofuranosyl) adenine (V) which comprises: reacting 2,6-di(trialkylsilylamino)-9-trialkylsilylpurine (II) with 2,3,5-tri-O-benzyl-1-chloro-D-arabinofuranose (III) wherein alkyl is a lower alkyl group containing 1 to 4 carbon atoms which can be straight chain or branched in a non-polar organic solvent to produce 2,6-di(trialkylsilylamino)-9-(2,3,5-tri-O-benzyl-beta-D-arabino-furanosyl)purine (IV) in a first reaction mixture; reacting (IV) with a lower alkanol containing 1 to 4 carbon atoms in a second reaction mixture to produce 2-amino-9-(2,3,5-tri-O-benzyl-beta-D-arabinofuranosyl) adenine (V); and separating (V) from the second reaction mixture.

The present invention also relates to the compound 2,6-di-(trialkylsilylamino)-9-(2,3,5-tri-O-benzyl-beta-D-arabinofuranosyl)purine produced in the process. Further, the present invention relates to a compound 2,6-di(trialkylsilylamino)-9-alkylsilypurine wherein alkyl is 1 to 4 carbon atoms, preferably one carbon atom (i.e. methyl).

Finally, the present invention relates to the process for the preparation of 2,6-di(trialkylsilylamino)-9-trialkylsilylpurine (II) which comprises: reacting 2,6-diaminopurine (I) with an excess of a compound selected from the group consisting of bis(trialkylsilyl) acetamide and hexaalkyldisilazane wherein alkyl contains 1 to 4 carbon atoms in the presence of ammonium sulfate; and providing (II) from the reaction mixture The preferred alkyl group contains one carbon atom (i.e. methyl), but can contain between 1 and 4 carbon atoms.

The non-polar solvent for the coupling reaction of (II) and (III) is preferably 1,2-dichloroethane. Other non-reactive organic solvents can be used.

The lower alkanol for removing the trimethylsilyl groups after the coupling reaction of (II) and (III) is methanol Other alkanols, such as ethanol, propanol or butanol, and containing 1 to 4 carbon atoms can be used. Use of a tertiary amine, preferably triethylamine, as an acid acceptor is desirable.

The reaction of (II) and (III) is preferably conducted at 80° to 85° C. which is reflux for dichloroethane. Preferably the reaction mixture is heated for at least 18 hours and preferably between 18 and 30 hours The removal of the silyl groups is usually conducted at a temperature of 50° to 60° C. for at least 30 minutes and preferably between 30 and 120 minutes This insures that the silyl groups are completely removed.

The compound (II) is prepared in a reaction mixture at a temperature between about 80° to 130° C. If necessary, a solvent is provided for the reaction, preferably acetonitrile with bis(trimethylsilyl) acetamide. Hexamethyldisilazane acts as its own solvent for the reaction. The reaction is conducted at between about 120° and 130° C. Preferably ammonium sulfate is provided in the reaction mixture as a catalyst.

Compound V is reacted with fluoroboric acid to replace the 2-amino group with a 2-fluoro group to provide 9-(2,3,5-tri-O-benzyl-beta-D-arabinofuranosyl)-2-fluoroadenine (VI). The benzyl groups are removed to provide 9-beta-D-arabinofuranosyl-2-fluoroadenine (VII) using a mixture of palladium chloride and hydrogen under pressure Preferably the pressure is between about 25 and 40 PSIG, and the temperature is between about 20° and 45° C. The solvent is preferably 2-methoxyethanol.

SPECIFIC DESCRIPTION

The reactions used in the following Examples 1 to 4 are:

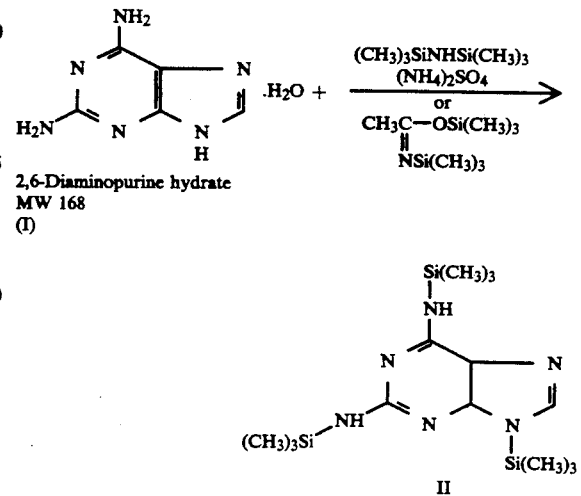

3

-continued 2,3,5-Tri-O-benzyl-1-O-p-nitrobenzoyl-beta-D-arabinose; Bn=benzyl 1-chlorosugar (III) (alpha, beta mixture)

Purine II + Chlorosugar III $\xrightarrow{\text{dichloroethane}}_{\text{Reflux}}$

IV

Compound IV $\xrightarrow{\text{CH}_3\text{OH}}$

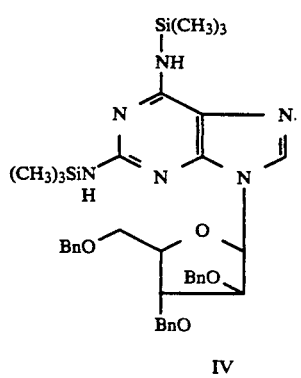

1) HBF$_4$, THF / NaNO$_2$, $-22°$ C.
2) NaOH
3) EtOAc

V (68%)
(MW 553)

$\xrightarrow{\text{H}_2/\text{PdCl}_2}$

VI (39%)
(MW 556)

4

-continued

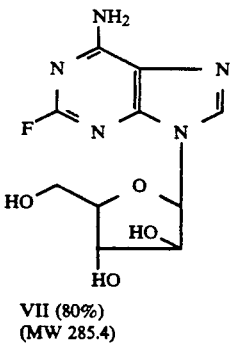

VII (80%)
(MW 285.4)

PREPARATION OF 2-AMINO-9-(2,3,5-TRI-O-BENZYL-BETA-D-ARABINOFURANOSYL)ADENINE (V)

Example 1

2,6,9-Tri(trimethylsilyl)-2,6-diaminopurine (II)

A mixture of 2,6-diaminopurine (I) (8.4g, 0.05 mole), hexamethyldisilazane (80 mL) and ammonium sulfate (200 mg) was heated at reflux with stirring until a clear solution was obtained (ca. 2 hours). Excess HMDS was evaporated (aspirator) and the residual syrup was used as such in the coupling reaction.

2-Amino-9-(2,3,5-tri-O-benzyl-beta-D-arabinofuranosyl) adenine (V)

The chlorosugar (III), obtained from 29 g of 1-O-p-nitrobenzoyl-2,3,5-tri-O-benzylarabinose, was dissolved in dry dichloroethane (80 mL, EDC) and this solution was added in one portion to the silyl derivative (II). The clear solution was heated to reflux and a portion of the EDC (20 mL) was distilled. The solution was heated at reflux for 18 h and additional EDC (30 mL) was distilled. Methanol (30mL) was added and the solution was heated at reflux for 15 min. The resulting suspension was concentrated to dryness and the residual solid was heated at reflux with fresh methanol (100 mL) The cooled suspension was diluted with ether (100 mL) and the solid was filtered and washed with ether to afford crude product (20.2 g). This material was dissolved in hot THF (300mL), filtered through Celite and concentrated to dryness. The residue was stirred with hot methanol (50mL), cooled, and diluted with ether and filtered to afford pure (V), 17.5 g; mp 159°-161° C. in 65% yield A mixture melting point with authentic material showed no depression.

Example 2

The above procedure of Example 1 was repeated with silyl derivative (II) prepared by providing a mixture of 2,6-diaminopurine (I) (3.36 g, 0.02 mol), bis(-trimethylsilyl)acetamide (16.2 g, 20 mL) in dry acetonitrile (20 mL) which was heated at reflux with stirring until a clear solution was obtained (ca. 1 hour). The acetonitrile and excess BTSA were removed (aspirator) and the residual syrup was used as such in the coupling reaction The yield of product V was 72% with the same melting point.

Example 3

2-Amino-9-(2,3,5-tri-O-benzyl-beta-D-arabinofuranosyl) adenine (V)

The chlorosugar (III), obtained from 29 g of 1-O-p-nitrobenzoyl-2,3,5-tri-O-benzylarabinose, was dissolved in dry dichloroethane (100 mL, EDC) and this solution was added in one portion to the silyl derivative II prepared by the method of Example 1. The chlorosugar (III) containing flask was rinsed with EDC (50 mL) and this was also added to the reaction mixture The clear solution was heated to reflux and a portion of the EDC (ca. 50 mL) was distilled. The solution was heated at reflux for 18 h. The solvent was evaporated under reduced pressure. Methanol (120 mL) was added to the residue and the solution was heated at reflux for 30 min. The reaction mixture was seeded with authentic material and allowed to sit overnight. The mixture was then cooled in an ice-bath (ca. 2° C.) for 1 hr and the product was filtered, washed with methanol (2×10 mL) and petroleum ether (2×20 mL) to afford (V) (18.7 g) mp 159°-161° C. in 65% yield. A mixture melting point with authentic material showed no depression.

Example 4

The procedure of Example 3 was repeated with the silyl derivative (II) prepared by the method of Example 2. The yield was 72%, with the same melting point.

The method of Examples 3 and 4 were preferred. No recrystallization was needed and the product was produced by seeding.

On a large scale, a tertiary amine can be added as an acid acceptor. This minimizes cleavage of the nucleoside product (V). This is shown by the following Example 5.

Example 5

2-Amino-9-(2,3,5-tri-O-benzyl-beta-D-arabinofuranosyl) adenine (V)

The crude chloro sugar obtained from 59 g of 1-O-p-(nitrobenzoyl)-2,3,5-tri-O-benzyl-D-arabinose was dissolved in 1,2-dichloroethane (EDC, 300 mL) and this solution was added to the silyl derivative II obtained from 16.8g of 2,6-diaminopurine prepared via the method of Example 1 (hexamethyldisilazane procedure). The flask was rinsed with additional (2×50 mL) EDC. The clear reaction mixture was heated at gentle reflux while a portion of the EDC (100 mL) was distilled. The reaction mixture was heated at reflux for 20 hours. A portion of the EDC (100 mL) was removed under aspirator pressure. The solution was cooled (ice-bath) and treated with triethylamine (10 mL) followed by methanol (200 mL). The solution was heated at reflux for 30 minutes and evaporated to dryness under reduced pressure. Fresh methanol (300 mL) was added and the mixture was stirred at room temperature overnight. The mixture was cooled to 0°-5° C. (ice-water bath) for one hour. The solid was filtered, washed with cold methanol (2×50 mL) and petroleum ether (2×50 mL) to yield the title compound (V), 40 g (72%), mp 159°-161° C.

It is intended that the foregoing description be only illustrative of the present invention and that the present invention be limited only by the hereinafter appended claims.

We claim:

1. A process for the preparation of the compound 2-amino-9-(2,3,5-tri-O-benzyl-beta-D-arabinofuranosyl)adenine (V) which comprises:
   (a) reacting 2,6-di(trialkylsilylanino)-9-trialkylsilylpurine (II) with 2,3,5-tri-O-benzyl-1-chloro-D-arabinofuranose (III) wherein alkyl is a lower alkyl group containing 1 to 4 carbon atoms which can be straight chain or branched in a non-polar organic solvent selected from the group consisting of 1,2-dichloroethane and acetonitrile at 80° to 85° C. for at least 18 hours to produce 2,6-di(trialkylsilylamino)-9-(2,3,5-tri-O-benzyl-beta-D-arabinofuranosyl)purine (IV);
   (b) reacting (IV) with a lower alkanol containing 1 to 4 carbon atoms in a second reaction mixture at between about 50°-60° C. for at least 30 minutes to produce 2-amino-9-(2,3,5-tri-O-benzyl-beta-D-arabinofuranosyl) adenine (V); and
   (c) separating 2-amino-9-(2,3,5-tri-O-benzyl-beta-D-arabino-furanosyl)adenine (V) from the second reaction mixture wherein the yield is at least 65% based upon the purine (II).

2. The process of claim 1 wherein the organic solvent is 1,2-dichloroethane which is present as the solvent in the first and second reaction mixtures and wherein the lower alkanol is methanol.

3. The process of claim 1 wherein after 2-amino-9-(2,3,5-tri-O-benzyl-beta-D-arabinofuranosyl)adenine (V) is provided in step (b), the second reaction mixture is seeded and then cooled so that (V) is precipitated from the second reaction mixture.

4. The process of claim 1 wherein alkyl is a methyl group.

5. The process of claim 3 wherein alkyl is methyl.

6. The process of claim 1 wherein triethylamine is added in step (b).

* * * * *